ical patent

United States Patent [19]
Samuels

[11] Patent Number: 6,030,396
[45] Date of Patent: Feb. 29, 2000

[54] DEVICE FOR REMOVING BLOOD VESSELS FROM THE HUMAN BODY

[76] Inventor: Peter B. Samuels, 14708 Sutton St., Sherman Oaks, Calif. 91403

[21] Appl. No.: 09/044,955

[22] Filed: Mar. 20, 1998

Related U.S. Application Data

[63] Continuation of application No. 08/857,350, May 16, 1997, Pat. No. 5,843,104, which is a continuation of application No. 08/561,250, Nov. 21, 1995, abandoned.

[51] Int. Cl.[7] .................................................. A61B 17/22
[52] U.S. Cl. ............................................................. 606/159
[58] Field of Search ..................................... 606/159, 149

[56] References Cited

U.S. PATENT DOCUMENTS

| | | | |
|---|---|---|---|
| 2,779,334 | 1/1957 | Sandborn | 606/159 |
| 3,568,677 | 3/1971 | Nolan et al. . | |
| 3,764,427 | 10/1973 | Reimels | 606/159 |
| 3,788,325 | 1/1974 | Jacobsen . | |
| 4,493,321 | 1/1985 | Leather | 606/159 |
| 4,798,586 | 1/1989 | Stevens | 606/194 |
| 4,952,215 | 8/1990 | Ouriel et al. | 606/159 |
| 5,026,383 | 6/1991 | Nobles | 606/159 |
| 5,047,041 | 9/1991 | Samuels | 606/159 |
| 5,106,363 | 4/1992 | Nobuyoshi | 606/194 |
| 5,141,491 | 8/1992 | Bowald | 606/159 |
| 5,141,503 | 8/1992 | Sewell | 606/159 |
| 5,304,189 | 4/1994 | Goldberg et al. | 606/159 |
| 5,395,384 | 3/1995 | Dutholt | 606/159 |
| 5,415,636 | 5/1995 | Forman | 606/101 |

FOREIGN PATENT DOCUMENTS

| | | | |
|---|---|---|---|
| 537676 | 12/1976 | U.S.S.R. | 606/159 |

*Primary Examiner*—Michael H. Thaler
*Attorney, Agent, or Firm*—Piper Marbury Rudnick & Wolfe

[57] ABSTRACT

A surgical instrument and method for using it for invaginate stripping of vericose veins from the human body utilize an elongate flexible tube provided with a pair of perforations at its distal end. The perforations provide for delivery of vasodilator fluid from within the tube to the vein lumen to dilate constricted portions of the vein and allow the inverted portion of the vein to pass therethrough. The perforations also provide for the attachment of sutures to the instrument and for the attachment of a stripper head to the instrument when necessary to retrieve a vein the tears during invaginate stripping.

3 Claims, 6 Drawing Sheets

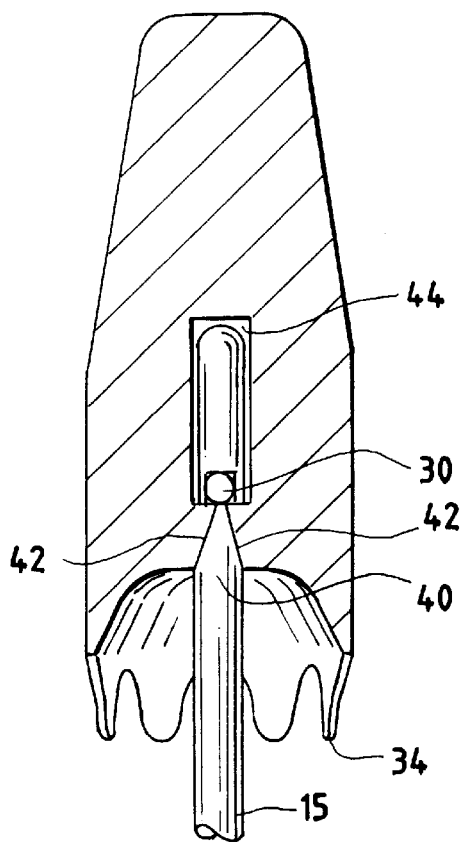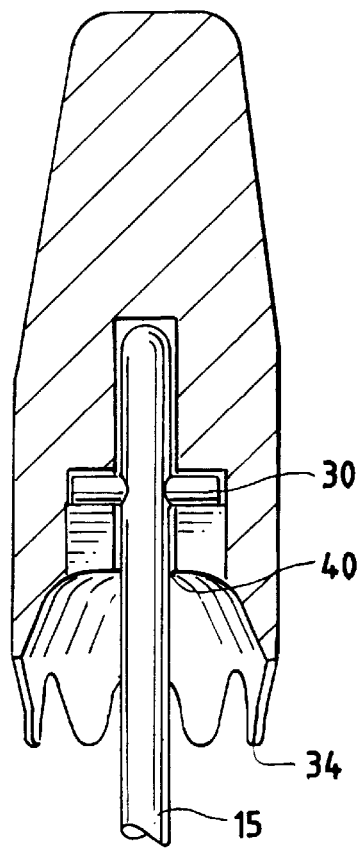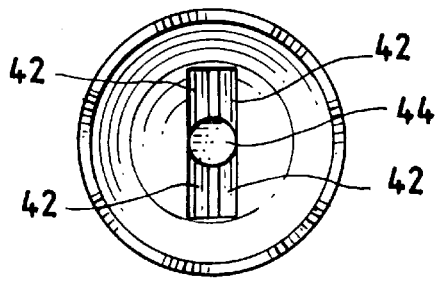

DEVICE FOR REMOVING BLOOD VESSELS FROM THE HUMAN BODY

This application is a continuation of application Ser. No. 08/857,350 filed May 16, 1997 now Pat. No. 5,843,104 which is a continuation of Ser. No. 08/561,250, filed Nov. 21, 1995, abandoned.

FIELD OF THE INVENTION

The invention relates generally to surgical instruments and methods for their use. Specifically, the invention relates to a surgical instrument for removing blood vessels, especially varicose veins, from the human body, and to a method for using such an instrument.

BACKGROUND OF THE INVENTION

Varicose veins, because of their cosmetically undesirable consequences, are a condition for which patients have sought surgical treatment. Surgical treatment of varicose veins typically involves the removal of a substantial portion, if not all, of the varicose vein, from the body. The most frequently removed vein is the large saphenous vein, which returns blood from the ankle upward along the leg.

Removal of the saphenous vein typically involves exposing it with an incision in the groin area, and severing the saphenous vein at its junction with the deeply located femoral vein. The saphenous vein is also exposed near the ankle or the knee by another incision. The prior art teaches various surgical techniques for stripping varicose veins, each with its own benefits and disadvantages. The primary objective with all stripping procedures is to ensure complete removal of the vein, while minimizing trauma to the surrounding perivenous tissues.

One prior art stripping technique involves the use of a ring, sized slightly larger than the diameter of the vein trunk, placed around the trunk and passed downward, using a rigid rod, until the ring encounters a vein branch. As it travels downward, the ring loosens the perivenous tissue from the vein. An incision is then made in the skin at the point at which the ring is palpated to expose the vein. The vein is brought to the surface and ligated. Now the loosened portion may be removed. The procedure repeats for the next vein portion and continues until the desired length of the vein has been removed. This method is disadvantageous because it requires a number of small incisions in order to divide and ligate the branches. These effects are cosmetically undesirable. Moreover, the technique is time consuming and tedious because it requires a number of different sized rings, which must be separately installed to efficiently strip varying diameters of vein segments as the operation proceeds. Although the use of the ring to loosen the vein results in effective saphenectomy, or vein removal, there is increased trauma to the perivenous tissue and thus increased post-operative discomfort to the patient. Multiple branches of the saphenous vein may necessitate additional incisions to divide the branches. The method also results in fracture of the main vein trunk causing excessive bleeding and difficulty in removing the main trunk. External stripping is thus outmoded.

Prior art techniques also include internal stripping, which involves cannulation, or insertion into the lumen of the vein, of a tool. The tool typically takes the form of a blunted string-like wire which is semi-flexible to permit navigation of the vein lumen. The wire is usually inserted into the vein from below and passed upward in order to minimize interference from the valves within the vein. For example, the Babcock/Meyers intraluminal stripping method involves the installation of a stripping head on the end of the rod once it emerges from the distal end in the vein. The stripping head is acorn-shaped and provided with a blunt edge which removes the vein by pure traction, in a sense, ripping the vein out by force. The stripping head is then pulled downward by traction on the wire and strips the vein from the surrounding perivenous tissue. Vein branches are usually torn of as they are encountered by the stripper. With this method, as a result of the taper of the saphenous vein from a large diameter down to a small diameter as one proceeds from the groin to the ankle, the entire saphenous vein trunk accumulates at the stripper head as it is drawn downward. The passage of this "bundle" of accumulated vein tissue downward through the perivenous tissues results in significant trauma and post-operative discomfort to the patient.

Vein stripping by invagination is another internal stripping technique of the prior art illustrated in FIGS. 1A–1D. This technique involves the attachment of the vein wall to a suitably shaped rod or braided wire 70. After the rod or wire 70 is cannulated, the distal end of the vein is attached to it with suture material 74. The distal end of the vein is then drawn closed with a suitable knot 78 in the sutures as shown in FIG. 1B. The vein wall is then inverted upon itself, quite similar to the way a sock would be turned inside out, so that the outer surface 80 of the vein travels downward within the vein lumen and becomes an inner 82 surface as shown in FIG. 1C. The venous tissue thus peels away from surrounding perivenous tissue 84, minimizing trauma to the patient.

Vein stripping by invagination has two major disadvantages. First, the taper of the saphenous vein results in the large upper end of the vein being inverted down through the narrower lower portion. Referring to FIG. 1D, as the stripping proceeds, travel of the large inverted end of the vein may meet with increased resistance within the vein lumen. Moreover, constriction 90 of the vein lumen, because of thick-walled or spastic portions, will obstruct travel of the inverted portion, thereby complicating to surgical procedure. Typically, invaginate stripping may be limited to small portions of the saphenous veins, instead of removing the vein in a single stripping step. For example, perforate-invaginate stripping (PIN) as described by Goren and Yellen in the *Journal of Vascular Surgery*, Volume 20, Number 6, pp. 970–77, involves a specially designed instrument that enables perforation of the vein wall from within and invagination of a portion of the saphenous vein through the perforation. One end of the tool is provided with a blunt head for grasping the traction sutures. The opposite end of the tool is provided with a groove for indicating the orientation of an angled segment of the tool which is rotated within the vein and used to perforate the vein wall. The short segment of the vein is then removed after it is inverted and invaginated upon itself.

The second major disadvantage of this stripping techniques is that the inverted portion of the vein may tear during the stripping operation. Frequently, strong branches of the main trunk of the saphenous vein will not sever as the main trunk is inverted and peeled away from the branch. Instead, the inverted portion of the vein tears because the junction between the branch and the main trunk is stronger than inverted portion. The severed portion of the inverted vein remains attached to the stripping rod or wire and will emerge at the lower incision in the vein when the rod or wire is withdrawn. The remaining portion, however, must first be located, and then retrieved by other stripping methods, usually involving additional incisions in the skin, additional scars on the body, and increased trauma to the patient.

Thus, while stripping by invagination results in less trauma than the Babcock/Meyers method, it is less effective in facilitating successful stripping of varicose veins. For this reason, use of the invaginate method is less favored in the vascular surgery field than the Babcock/Meyers stripping technique. There is thus a need for a surgical instrument and technique which improves the effectiveness of the invaginate vein stripping method and which facilitates easy change-over to the Babcock/Meyers type stripping operation in the event of unsuccessful stripping using the invaginate stripping method.

SUMMARY OF THE INVENTION

The present invention improves upon the prior art by providing a surgical instrument with three major improvements. First, a surgical instrument is provided having means to convey fluid or fluid containing a vasodilator into the vein lumen to dilate the vein during the invaginate stripping operation, thereby eliminating obstructions to the inverted portion of the vein as it proceeds past constricted or spasmatic areas. Second, a surgical instrument is provided with means for the attachment of sutures to the instrument to facilitate the invaginate stripping operation. Third, a surgical instrument is provided with means for quickly attaching a stripper head thereto in order to retrieve a torn vein portion.

A preferred embodiment of the present invention is constructed as an elongate tube having a pair of perforations at a distal end thereof. The perforations are diametrically opposed on the body of the tube and form a transverse hole which communicates with the inner cavity of the tube. The perforations provide a triple function. First, the perforations permit the attachment of sutures to the tube to facilitate the invaginate stripping of the vein body. Second, the perforations convey fluid, which may include a vasodilator, into the vein lumen to dilate constricted portions of the vein. Third, a stripper head may be attached to the tube body using a small rod disposed in the perforations in order to retrieve a torn vein portion which has severed during the invaginate stripping operation. The present invention is also embodied in the method of using the above described instrument and in the stripper head construction which facilitates attachment to the rod disposed in the tube.

DESCRIPTION OF THE DRAWINGS

FIGS. 3A–3C illustrates the details of a preferred embodiment of the stripper head of the present invention.

Figure 1A:
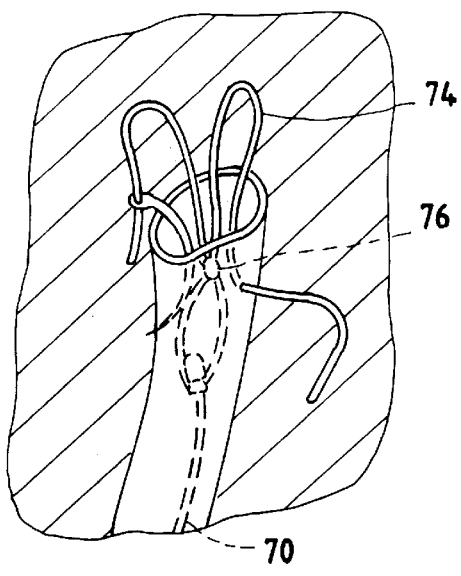
FIGS. 1A–1D depict one of the prior art devices and the prior art method for invaginate vein stripping.

The foregoing and other features and advantages of the present invention will become more apparent in light of the following detailed description as illustrated in the accompanying drawings.

DESCRIPTION OF THE PREFERRED EMBODIMENTS

Referring to FIG. 2, a preferred embodiment of the present invention comprises an elongate tubular body 15 having an interior cavity 13 running substantially along its length. The instrument body is provided at its distal end with a rounded bullet-shaped tip 12 which facilitates cannulation, or insertion of the instrument into the vein lumen. Near the rounded tip 12 there is provided a fluid delivery means in the form of a pair of perforations 14 which communicate with cavity 13 in order to deliver fluid from cavity 13 to the vein lumen. Perforations 14 are diametrically opposed on the tube body. At the end of the body opposite the bullet-shaped head 12, there is provided a means for introducing fluid into the cavity as well as a means for retaining fluid therein. These means may comprise a Luer lock 20, which releasably couples a syringe to the instrument for the introduction of fluid, and a stopcock 16 which are disposed on the tube in communication with cavity 13. Luer lock 20 and stopcock 16 and their function are well-known to those of ordinary skill in the art.

Instrument body 15 may be constructed of any material which provides sufficient rigidity and compressive strength to permit insertion of the tool into the blood vessel and sufficient flexibility to permit navigation of the tool of the tortuous path associated with the vein lumen, including surgical metal or plastic. Suitable materials for the construction of the tube 15 may comprise nylon or Teflon or other polymers or polycarbonates such as MAKROLON and the tube may incorporate carbon fiber or wire reinforcement to provide a composite, kink-resistant, structure. Body 15 is preferably of an outer diameter of about 1.0 to 1.5 millimeters. Cavity 13 of the instrument is preferably about 0.8 mm in diameter, leaving a tube wall thickness of about –0.2 mm. Perforations 14 are preferably of a diameter of about 1–1.3 mm and are preferably located approximately 1.5 centimeters from the tip of blunted end 12. The length of the tool from the tip 12 to the Stopcock 16 and Luer-lock 20 will vary depending on the application and particular surgical operation. For example, in applications involving removal of the entire saphenous vein, a length of approximately 110 centimeters is preferable.

Figure 2A:
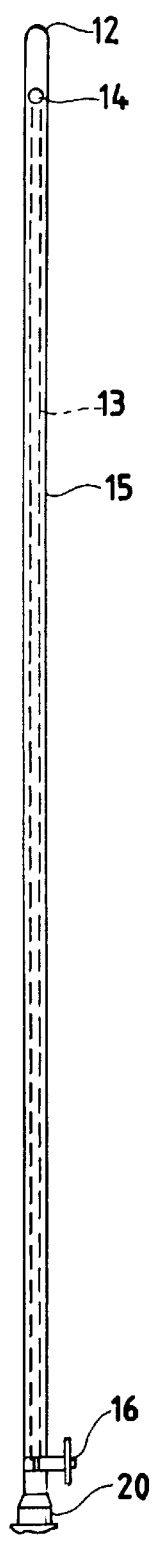
FIGS. 2A–2D illustrate front and side views of a preferred embodiment of the tool body of the present invention.
Figure 2B:
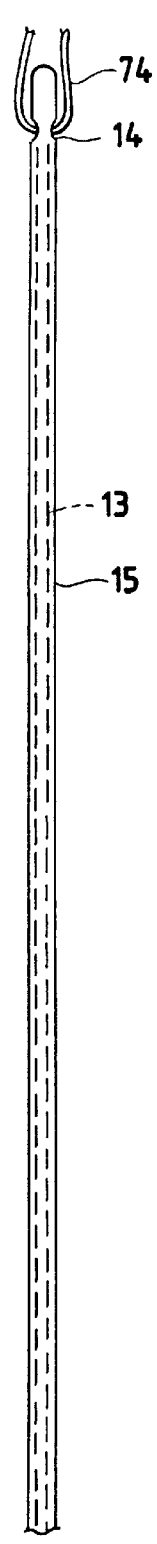
Figure 2C:
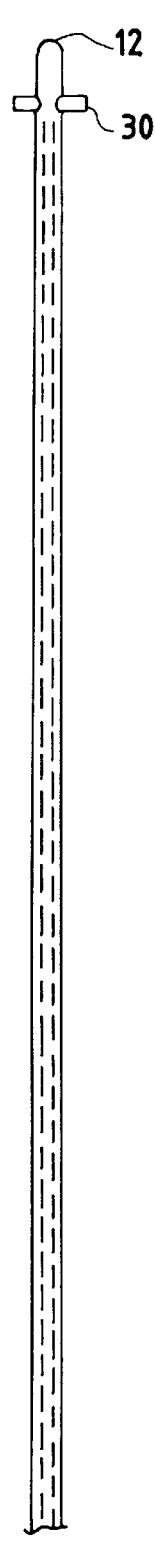
Figure 2D:
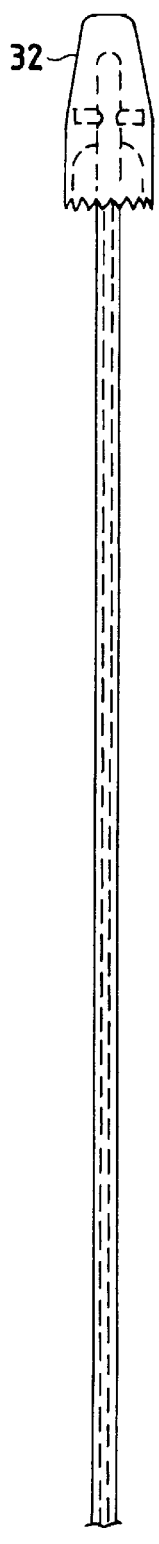

As illustrated in FIG. 2B, perforations 14 provide a means on body 15 to attach traction suture elements 74. Traction sutures 74 follow the inverted portion of the vein through the vein lumen and become necessary to retrieve a portion of the inverted vein should it tear during the stripping operation, as will describe below. As illustrated in FIGS. 2C and 2D, perforations 14, in addition to delivering fluid from the interior cavity 13 to the vein lumen, also facilitate attachment of stripper head 32 to the end of the instrument. Rod 30, which may be constructed of plastic or metal, is disposed in the tube 15 and disposed through perforations 14. The stripper head 32 is provided with a slotted connection adapted to receive and retain the rod portion 30, as will be described below.

FIGS. 3A–3C, illustrate a preferred embodiment of the stripper head of the present invention. As shown in FIG. 3A, stripper head 32 is provided with a snap fitting for attaching it to tube 15 via rod 30. Hole 44 is adapted to receive the end of tubular body 15 and semi-flexible slot 40 is adapted to receive rod 30. Semi-flexible slot 40 is provided by forming a pair of resilient catches 42 disposed therein on each side of the hole 44 as shown in FIG. 3C. Semi-flexible slot 40 is so dimensioned such that insertion of the rod element 30 into the flexible slot 40 causes slight resilient deformation of the catches 42. As shown in FIG. 3A, full insertion of the rod past the catches 42 causes them to snap back into position thereby retaining the rod element within the semi-flexible slot 40.

Stripper head 32 is typically constructed of metal and the outer shape thereof includes a serrated bottom edge 34 which is adapted for the removal of venous tissue during the stripping operation. The details of the semi-flexible slot 40 may be formed integrally with the metallic stripper head, or, in the alternative, may be provided on a plastic insert (not shown) which may be fixably fastened into a complementarily-shaped recess in the metal stripper head. The general shape of the stripper head is well known in the prior art and is described in U.S. Pat. No. 5,047,041 which was issued to the present inventor and which is hereby incorporated by reference. The snap fitting illustrated in FIGS. 3A through 3C permits the quick installation of the stripper head on the rod element from above after the rod element has been reinserted through the blood vessel and emerges through the severed end thereof.

Figure 4A:
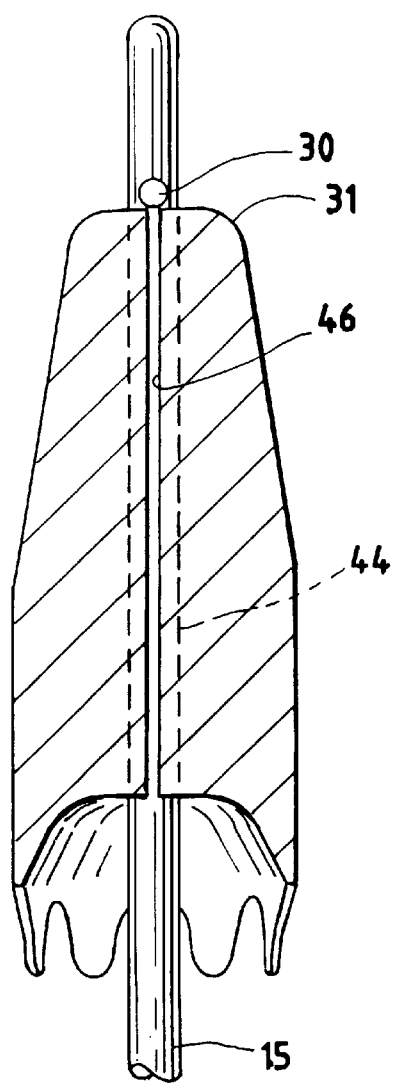
FIG. 4 illustrates the details of another preferred embodiment of the stripper head of the present invention.
Figure 4B:
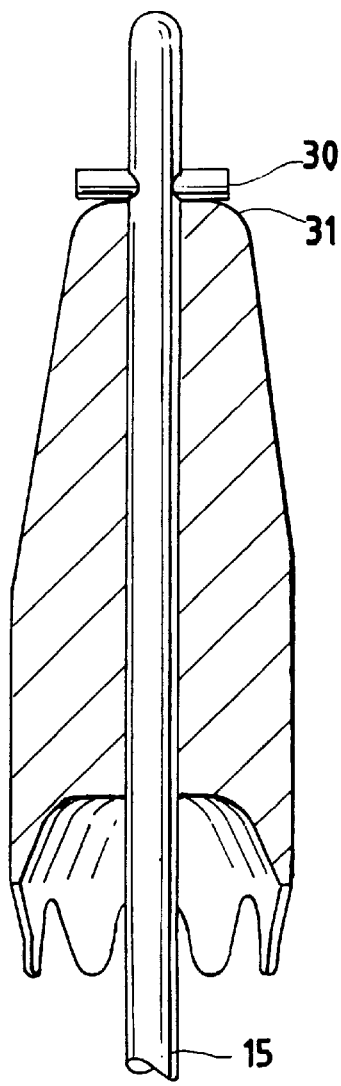
Figure 4C:
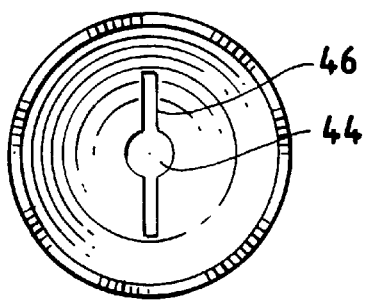

FIGS. 4A through 4C illustrate another embodiment of the stripper head of the present invention, Stripper head 32 is provided with slot 46 and hole 44 which run through the body of the stripper head longitudinally along its length. Slot 46 is configured to sidably receive rod element 30 and hole 44 is configured to receive the tool body 15. Stripper head 32 is installed on the body portion 15 from above by aligning slot 46 with rod 30 and pushing downward on the stripper head, thereby causing rod 30 and body 15 to slide upwards within stripper head 32 until rod 30 emerges through the tip 31 of the stripper head. Stripper head 32 is then fastened to body 15 with a simple twisting motion of the body 15 whereby rod 30 is no longer aligned with slot 46, thereby retaining stripper head 32 on the tube 15. The stripper head may then be drawn downward by traction on the tool 15.

Figure 1B:
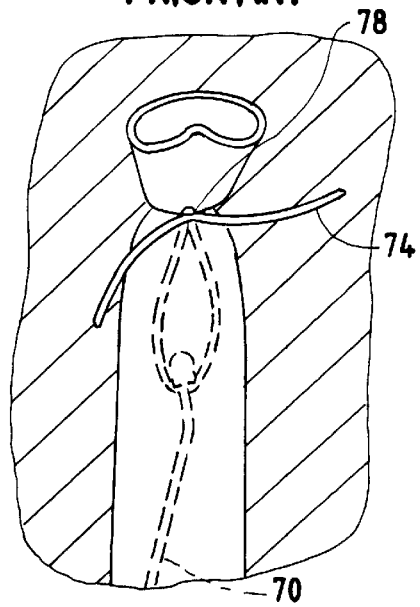
Figure 1C:
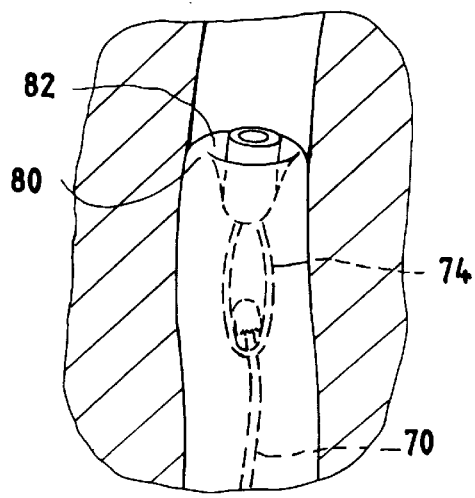
Figure 1D:
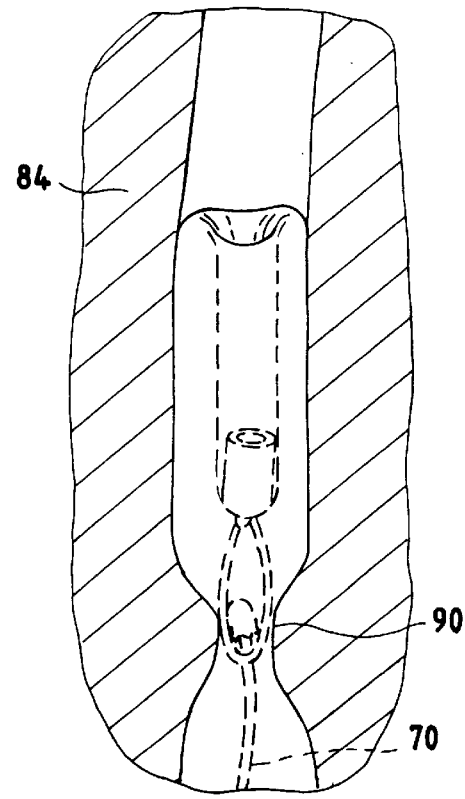
Figure 5A:
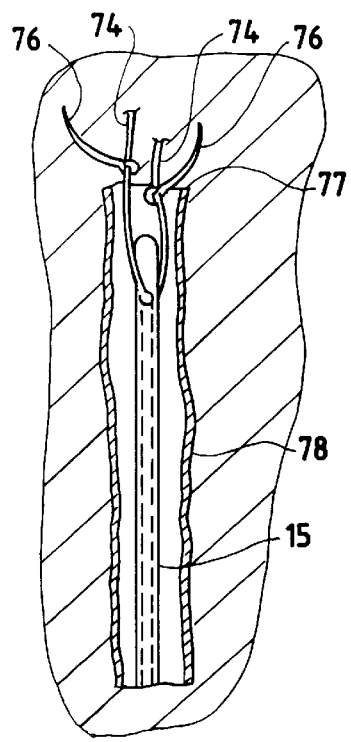
FIGS. 5A through 5F illustrate a method of use of a preferred embodiment of the present invention.

The method of use of a preferred embodiment of the present invention will now be described with reference to FIGS. 5 and 6. Referring to FIG. 5A, tool 15 of the present invention is shown inserted into vein 78. Traction sutures 74 are shown threaded through perforations 14. Traction sutures 74 emerge from the vein at ligated end 77 which, in the case of a stripping operation for the saphenous vein, results from severance of the saphenous vein at the femoral junction in the groin area. Insertion of the instrument 15 from below occurs at an incision (not shown) just below the knee or near the ankle. Needles 76 are threaded onto traction sutures 74 in preparation for fastening the traction sutures 74 to the vein wall. This fastening technique is known in the prior art and illustrated in FIGS. 1A and 1B as described above.

Figure 5B:
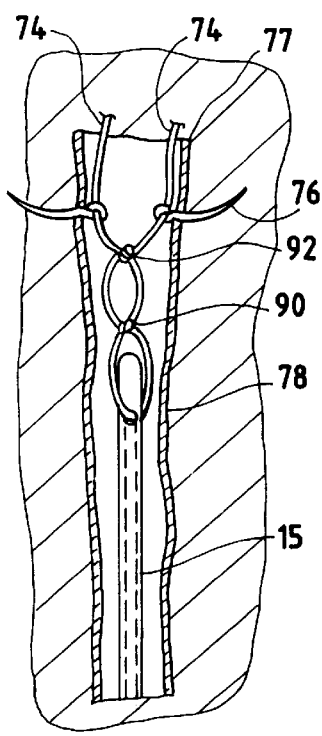
Figure 5C:
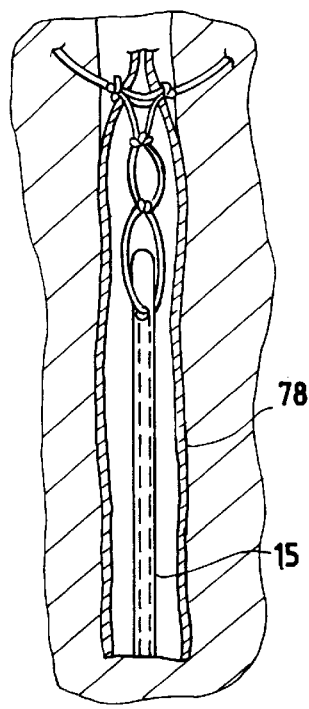

As illustrated in FIG. 5B, a floating knot 90 is made in the traction sutures 74 so as to form a loop in traction sutures fastening which is fastened through perforations 15. A second knot 92 in traction sutures 74 is made above the first knot 90. Traction sutures 74 are threaded through the vein wall at two locations and then looped around the outside of the vein and tied so as to draw the outer walls of the vein together as shown in FIG. 5C.

Figure 5D:
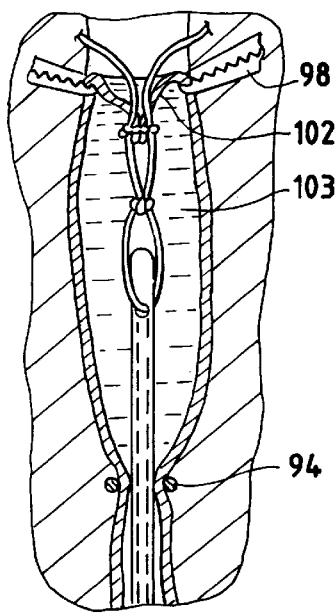
Figure 5E:
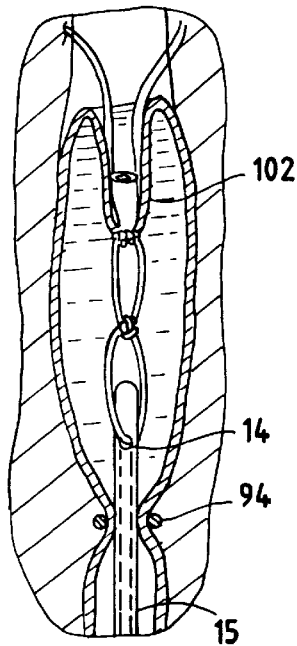

FIG. 5D illustrates the initiation of the inversion of the end of the vein. After the instrument 15 has been fastened to the vein wall and the outer walls drawn together, a fluid containing a vasodilator is injecting into the vein lumen. A VAS-LOOP or elastic band 91 is cinched around the vein and instrument to prevent outflow of the fluid. Fluid pressure permits invagination to occur easily. Traction or pulling force on the tool 15, while retaining the hemostats 98 in a fixed position, causes the drawn together portion of the vein to invert upon itself, forming an inverted portion 102 which is disposed in the vein lumen 103. Once the inversion has begun, the hemostats may be removed and further traction on the instrument 15 results in a peeling away of the venous tissue from the surrounding tissue and the subsequent inversion of the vein wall within itself as shown in FIG. 5E.

Traction sutures 74 follow the inverted portion 102 down through the lumen.

Figure 5F:
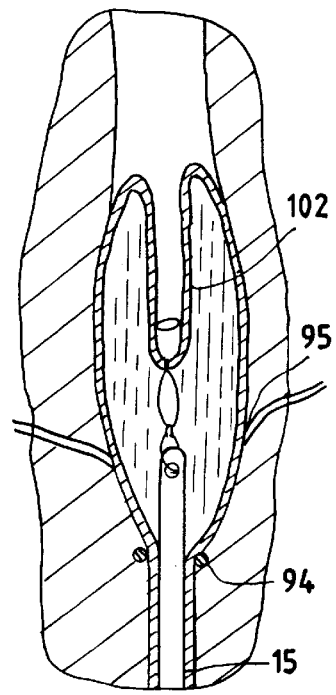

Referring to FIG. 5F, constricted areas 95 of the vein are expanded by the injection of fluid. Constriction may result from spasm or narrowness in the vein lumen. As an alternative to dilating the vein before invagination, dilation may occur after invagination has begun when the invaginated portion 102 encounters obstruction. When the inverted portion 102 of the vein wall becomes obstructed by constricted portion 95, the surgeon will sense a resistance to travel of the instrument 15 within vein. The vasodilator containing fluid is then introduced into the instrument cavity 13 via syringe inserted into Luer-lock 20. The vasodilator is infused into cavity 13 travels under slight pressure outward through perforations 14 into the vein lumen. Sufficient fluid pressure is applied to cause dilation of the vein and expansion of the constricted portion 95. The fluid pressure and vein expansion may be maintained using stopcock 16. The vein is no longer constricted and inverted portion 102 of the vein may pass through the vein lumen without obstruction. Fluid pressure in the vein lumen is gradually decreased by appropriately releasing the stopcock 16. The above-described procedure thus proceeds for each obstruction encountered during the inversion and stripping operation of the blood vessel. Notably, the tool of the present invention can be useful to irrigate the perivenous tissue following removal of the vein. Preferably, warm saline is infused through the tool to induce blood clotting in the tissue.

Figure 6A:
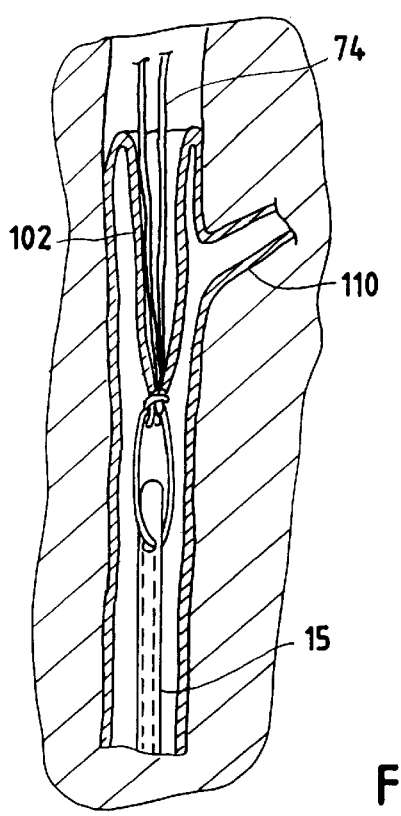
FIGS. 6A through 6F illustrate the method of use of a preferred embodiment of the present invention in retrieving a torn vein portion.
Figure 6B:
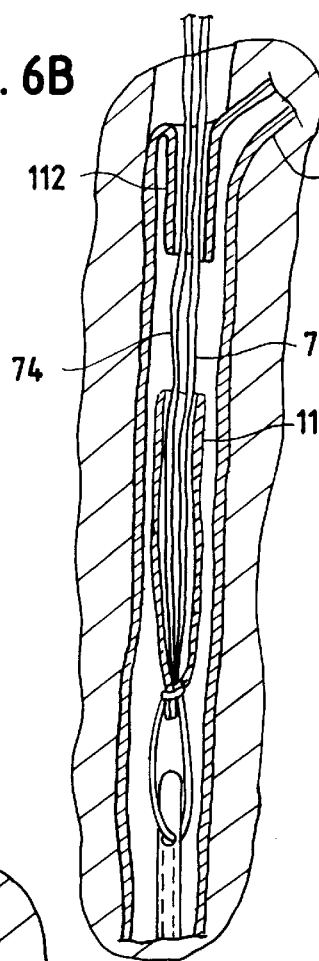

FIGS. 6A–6D illustrate the use of a preferred embodiment of the present invention in removing torn vein portions. Occasionally, during the inversion of the main trunk of the vein, a strong branch of the vein will be encountered and may result in the tearing of the inverted portion of the vein. FIG. 6A illustrates the inversion of a main trunk portion having a vein branch 110. FIG. 6B illustrates the inverted portion of the vein after it has severed because of the strength of the vein branch 110. There remains a vein portion 112 of the inverted vein which is attached to the vein branch 110 and a portion 114 of the inverted vein which remains attached to the tool 15. Because of the length of traction sutures 74, which is preferably at least twice as long as the length of the vein desired to be stripped, traction sutures 74 follow the tool downward as it proceeds through the stripping operation and become disposed within the inverted portion of the vein. Traction sutures 74 function to retrieve the instrument 15 in the event that the inverted portion 102 of the vein tears. Detached portion 114 of the vein is removed by pulling instrument tube 15 out through the vein bottom, removing the detached portion 114 of the vein, and re-tieing the traction sutures 74 onto the tube 15.

Figure 6C:
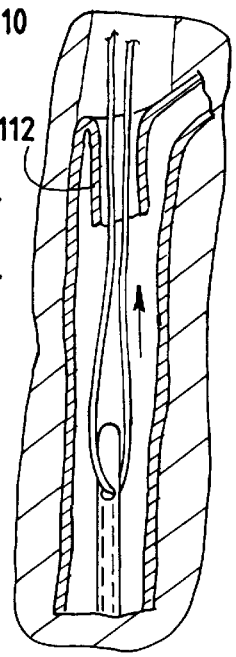
Figure 6D:
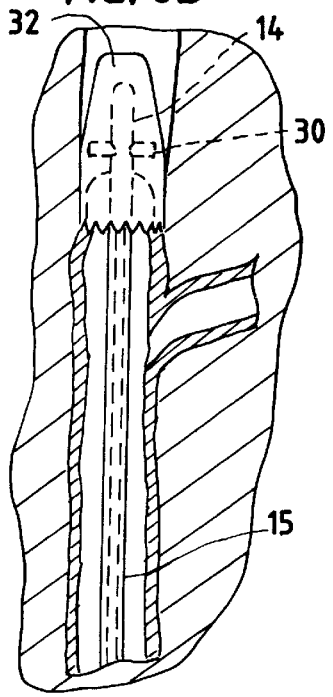
Figure 6E:
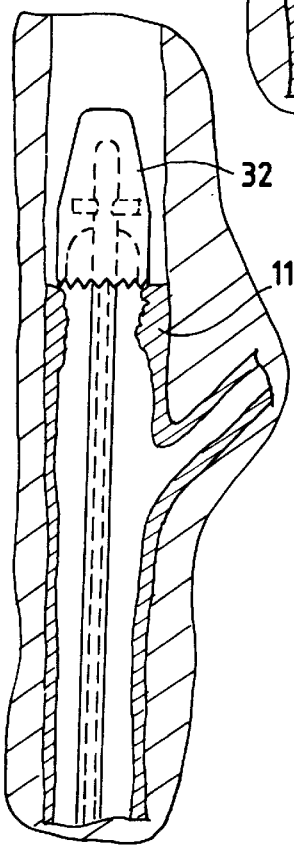
Figure 6F:
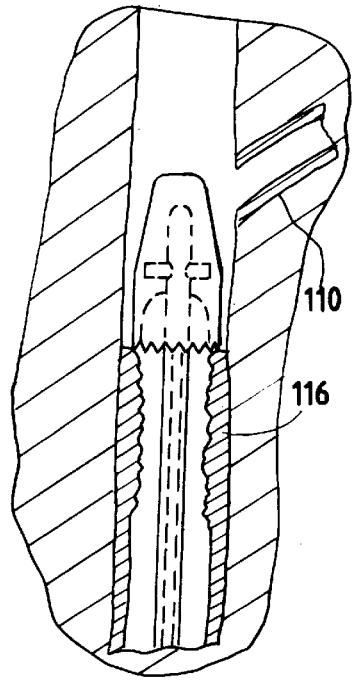

Referring to FIG. 6C, the instrument 15 is reinserted into the vein and retrieved using traction sutures until it emerges from the distal end of the vein above. At this point the remaining portion 112 of the vein may also emerge through the top of the ligated end of the vein and can be removed by scissors. As shown in FIG. 6D, rod 30 is installed through perforations 14 and stripper head 32 is attached to the top of the instrument 15. The instrument 15 and stripper head 32 are then pulled downward back through the vein to retrieve the portion 112 of the vein that was left due to the tearing. The vein tissue accumulates in a bundle 116 disposed below the stripper head 32 as it is drawn downwards as shown in FIG. 6E. As stripper head 32 passes the strong vein branch 110, the serrated edge of the stripper head severs the strong vein branch 110 from the main trunk. Stripping may then proceed along the remaining portion of the vein.

The vein stripping instrument of the present invention thus provides a triple function in that it permits attachment of the traction sutures thereto, irrigation and dilation of the interior of the blood vessel to expand constrictions therein, and the attachment of the stripping head in the event that a portion of the vein tears off during the stripping operation. There has thus been disclosed a new and useful device and method which improves upon the prior art. It should be understood that various modifications of the embodiments described above may be made without departing from the scope of the present invention as defined in the claims that follow.

What is claimed is:

1. In combination: a suture adapted to be attached to a ligated end of a blood vessel and a surgical instrument for invaginate stripping of the blood vessel from the human body, said instrument comprising an elongate tubular body being sufficiently rigid to permit insertion thereof into the lumen of the blood vessel but sufficiently flexible to follow the contours of the lumen and including:

a) a distal end having a solid and rounded bullet-shaped tip for facilitating insertion and travel of said tubular body within said lumen;

b) perforations through the tubular body proximate the distal end to which said suture is anchored to secure the ligated end of the blood vessel to the tubular body to permit invaginate stripping of the blood vessel, said perforations also sized larger than the suture and communicating with the interior of the tubular body for the delivery of fluid from the interior of the tubular body to the blood vessel to dilate the vessel lumen;

whereby constrictions in the blood vessel which would obstruct passage of the invaginated portion of the blood vessel through the blood vessel lumen are dilated by fluid pressure within said blood vessel lumen.

2. The surgical instrument of claim 1, further comprising a Luer-lok communicating with the interior of the tubular body providing for the injection of fluid into the interior of the tubular body and increasing fluid pressure within the lumen of the blood vessel.

3. The surgical instrument of claim 2, further comprising a stopcock disposed near a proximal end of the tubular body for retaining fluid therein and maintaining fluid pressure within the lumen of the blood vessel.

* * * * *